(12) United States Patent  (10) Patent No.: US 7,555,339 B2
Nielsen et al.  (45) Date of Patent: *Jun. 30, 2009

(54) CAPACITOR DESIGNS FOR MEDICAL DEVICES

(75) Inventors: Christian S. Nielsen, River Falls, WI (US); John D. Norton, New Brighton, MN (US); Mark E. Viste, Brooklyn Center, MN (US); Joachim Hossick-Schott, Minneapolis, MN (US); Anthony W. Rorvick, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 746 days.

This patent is subject to a terminal disclaimer.

(21) Appl. No.: 10/774,210

(22) Filed: Feb. 6, 2004

(65) Prior Publication Data

US 2005/0177193 A1 Aug. 11, 2005

(51) Int. Cl.
*A61N 1/39* (2006.01)
(52) U.S. Cl. .............................. 607/5; 607/36; 361/517
(58) Field of Classification Search ...................... 607/5, 607/33, 36–37; 361/500, 508–509, 503
See application file for complete search history.

(56) References Cited

U.S. PATENT DOCUMENTS

| | | | | |
|---|---|---|---|---|
| 4,830,940 A * | 5/1989 | Keister et al. ................. 429/94 |
| 5,131,388 A * | 7/1992 | Pless et al. ...................... 607/5 |
| 5,600,535 A * | 2/1997 | Jow et al. ..................... 361/503 |
| 5,715,133 A * | 2/1998 | Harrington et al. .......... 361/500 |
| 5,926,362 A * | 7/1999 | Muffoletto et al. .......... 361/503 |
| 6,130,005 A * | 10/2000 | Crespi et al. ................. 429/219 |
| 6,283,985 B1* | 9/2001 | Harguth et al. ................. 607/1 |
| 6,687,116 B2* | 2/2004 | Hudis .......................... 361/502 |
| 6,819,544 B1* | 11/2004 | Nielsen et al. .............. 361/508 |
| 6,850,405 B1* | 2/2005 | Mileham et al. ............ 361/302 |
| 6,995,971 B2* | 2/2006 | Norton et al. ................ 361/523 |
| 2003/0058606 A1* | 3/2003 | O'Phelan et al. ............ 361/509 |
| 2004/0243183 A1* | 12/2004 | Norton et al. ................... 607/5 |
| 2006/0023400 A1* | 2/2006 | Sherwood .................... 361/503 |

* cited by examiner

*Primary Examiner*—Carl H Layno
*Assistant Examiner*—Brian T Gedeon (57) ABSTRACT

A capacitor for use in implantable medical devices (IMDs) such as implantable defibrillators, implantable cardioverter-defibrillators, implantable pacemaker-cardioverter-defibrillators, and the like stores charge for use in the delivery of high voltage electrical therapy. The capacitor design can reduce capacitor volume significantly and may also improve charge holding capacity relative to conventional capacitor designs. Moreover, since capacitors typically comprise a significant portion of the volume of an IMD, significant reductions in capacitor volume can likewise significantly reduce the size of the IMD.

18 Claims, 7 Drawing Sheets

CAPACITOR DESIGNS FOR MEDICAL DEVICES

TECHNICAL FIELD

The invention relates to medical devices and, more particularly, to high voltage capacitors for storing energy in and delivering therapy from medical devices.

BACKGROUND

High voltage capacitors are commonly used in various medical devices in order to store charge so that electrical stimulation therapy (e.g., defibrillation and/or cardioversion) can be delivered to a patient. For example, defibrillators commonly make use of one or more high voltage capacitors to store charge prior to delivery of high voltage defibrillation therapy to a patient. Defibrillation electrical therapy can be delivered to depolarize the patient's heart and thereby overcome an episode of a potentially lethal arrhythmia (e.g., ventricular fibrillation).

Many different medical devices have been designed with defibrillation capabilities. Examples include the automatic external defibrillator (AED), implantable cardioverter-defibrillators (ICD) and the like. Capacitors are commonly used in such medical devices to store charge for delivery of cardiac defibrillation therapy and/or cardioversion therapy, and the like. Other types of medical devices, including medical devices not yet developed, may also implement high voltage capacitors for these or other applications.

Medical devices that provide defibrillation therapy typically include at least the following primary components: a power source, one or more capacitors, at least a pair of cardiac electrodes, and circuitry to control delivery of cardiac therapy. The capacitor(s) typically consume a significant portion of the volume of a medical device, particularly an IMD. Improved medical device capacitor designs are highly desirable, particularly for an ICD, to achieve size reductions strongly associated with patient acceptance and comfort, among other reasons.

SUMMARY

In general, the present invention provides improved high energy density capacitor apparatus and methods of fabrication therefore. Capacitors designed according to the present invention provide reduced capacitor volume as compared to the prior art and may also improve the charge storage capacity relative to prior art capacitor designs. Moreover, since capacitors typically comprise a significant portion of the volume of an ICD, reductions in capacitor volume likewise significantly provides an opportunity to further reduce the overall size of medical devices incorporating them.

The present invention provides a medical device including circuitry to control delivery of electrical therapy to a patient and at least one capacitor to store charge for use in the delivery of the electrical therapy. The capacitor may comprise a first anode member composed of powered metal that is fabricated in situ within a first encasement member, or shell. During such processing a desired quantity of a powdered metal such as tantalum is pressed, sintered and anodized, or "formed" (i.e., an oxide is grown on the surfaces of the member in the presence of a formation electrolyte) as is known in the art. Alternatively, the first anode member can be processed prior to placing it in the first encasement shell. According to the present invention a second anode member resides in a second encasement shell (again with processing occurring either in situ or prior to being placed into the second encasement shell). A cathode member is then sandwiched between the first and second anodes (within the first and second encasement shells) with, as necessary, suitable separator material disposed therebetween.

For all the embodiments of the present invention described herein, wherein more than one cathode member is desirable, a ratio of 2:1 (two anode members for each cathode member) is employed. Also, while not always specified herein, as is known in the art the anodes are typically electrically insulated from each cathode member with a thin separator sheet and the interior volume of the capacitor cell is filled with a suitable working electrolyte. While not specified or depicted herein each capacitor cell typically requires at least one electrical feedthrough coupled to either the pair (or multiple pairs) of anodes or each cathode and a fill port for admitting liquid electrolyte.

In another embodiment, the invention provides a medical device including circuitry to control delivery of electrical therapy to a patient and a capacitor to store charge for use in the delivery of electrical therapy. According to this embodiment, a capacitor has a single anode pressed, sintered and formed within a first electrically conductive encasement shell (or the single anode may be constructed and electrically coupled to the first encasement shell); a cathode constructed within (or on a surface portion of a second shell) or constructed and subsequently electrically connected to the second electrically conductive encasement shell; and an insulative material disposed at the interface of the first and second encasement shells to electrically isolate the shells (and thus the anode and the cathode) from each other.

In another embodiment, the present invention provides a capacitor comprising an anode formed within a first encasement shell, a cathode forming a second encasement shell, and electrically insulative material disposed at the interface of the first and second encasement shells to electrically isolate the anode from the cathode.

In another embodiment, the present invention provides a method comprising processing (i.e., pressing, sintering and forming) a quantity of tantalum powder into a first and a second tantalum encasement shell to define first and second anodes, applying a thin titanium substrate member with ruthenium oxide disposed on both sides to form a cathode, wrapping a non-conductive separator sheet around the cathode, and sandwiching the cathode between the first and second anodes to fabricate a single capacitor cell.

The details of one or more embodiments of the invention are set forth in the accompanying drawings and the description below. Other features, objects, and advantages of the invention will be apparent from the description and drawings, and from the claims.

DETAILED DESCRIPTION

The invention is directed to capacitor designs for capacitors of medical devices such as implantable cardioverter-defibrillators (ICDs) and to non-implantable devices such as manual or automated external defibrillators (AEDs). In the description that follows, primarily for convenience such medical devices are referred to as ICDs with the understanding that any cardiac defibrillation device is also covered thereby, including manual defibrillators and AEDs. Also, while most references to many of the details of the invention are provided in the context of a capacitor used to store charge for delivering defibrillation electrical therapy to a patient. The capacitor designs described herein, however, may find use in a wide variety of other device applications, including non-medical applications wherein high energy density and compact cell size are significant design constraints. That is, the present invention offers significant reduction in capacitor cell volume, and thus, may be most useful in applications where size is a primary concern.

Figure 1:
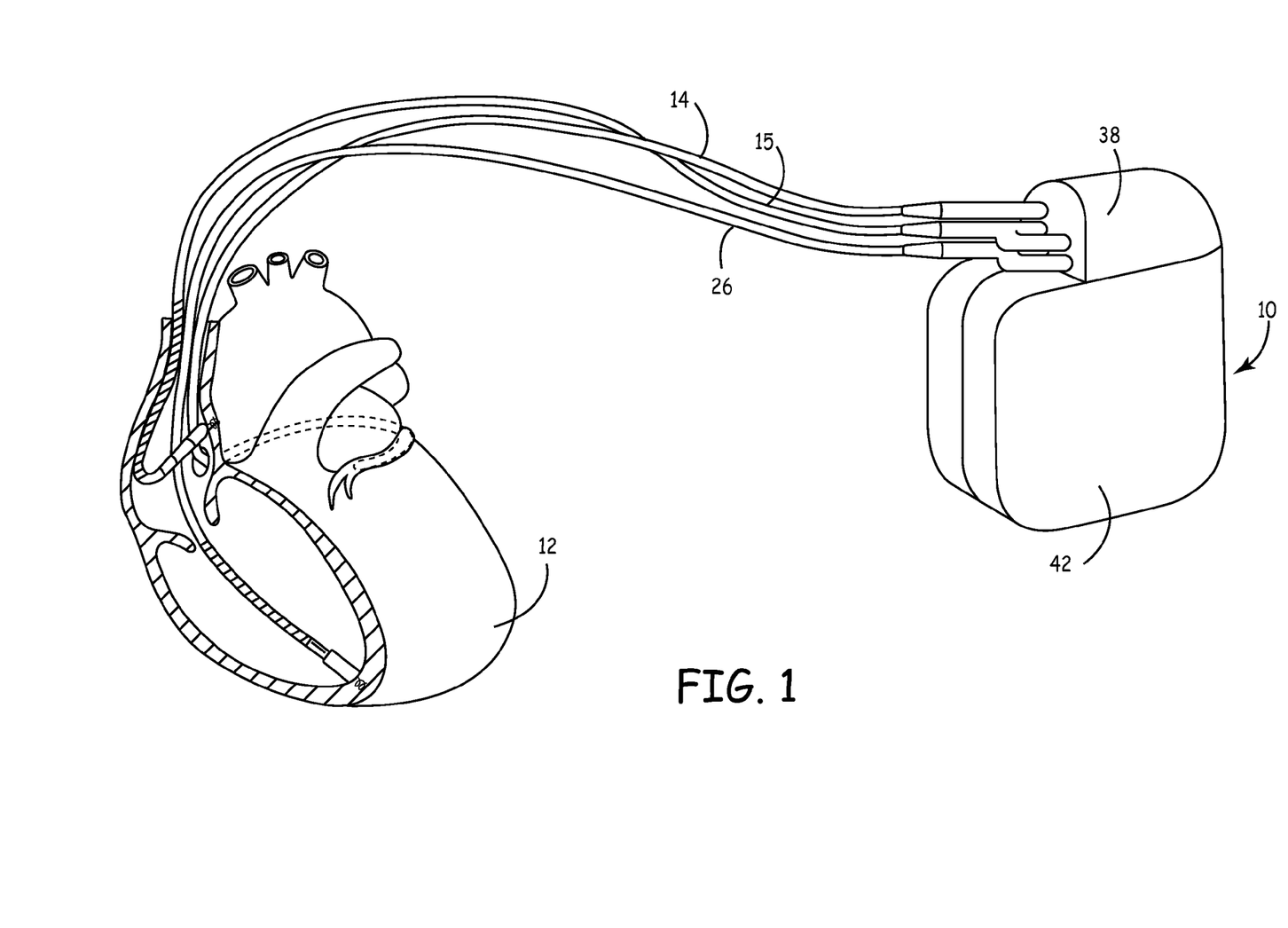
FIG. 1 is a schematic representation of an exemplary medical device such as an ICD, which can implement a capacitor design in accordance the invention.

FIG. 1 is a schematic representation of an exemplary IMD 10 implementing one or more aspects of the invention. In this case, IMD 10 is a three channel pacing device shown in conjunction with a human heart 12. IMD 10 also includes cardioversion and defibrillation functionality and may be referred to as a pacemaker-cardioverter-defibrillator. IMD 10 includes a capacitor that, as outlined in greater detail below, can achieve reduced volume relative to various conventional capacitors. As mentioned above, the invention may also find application in numerous other types of IMDs or external medical devices.

As shown in FIG. 1, IMD 10 includes left ventricular (LV) coronary sinus lead 14, which is passed through a vein into the right atrium of heart 12, into the coronary sinus and then inferiorly in the great cardiac vein and cardiac veins extending from the great vein to extend the distal ring pace/sense electrodes alongside the LV chamber. The distal end of LV coronary sinus lead 14 positions ring electrodes optimally with respect to the adjacent wall of the left ventricle. Right ventricular (RV) lead 26 is typically passed through either the superior or inferior vena cava that leads into the right atrium and feeds into the right ventricle where its distal ring and tip pace/sense electrodes are fixed in place in the apex, RV outflow tract or in the interventricular septum, or the like. Right atrium (RA) lead 15 is positioned within the RA chamber, with distal end of RA lead 15 positioning ring electrodes optimally with respect to the adjacent wall of the right atrium or positioned within the RA appendage. The different leads may include electrodes for pacing and also high voltage coil electrodes for cardioversion or defibrillation therapy.

Figure 2:
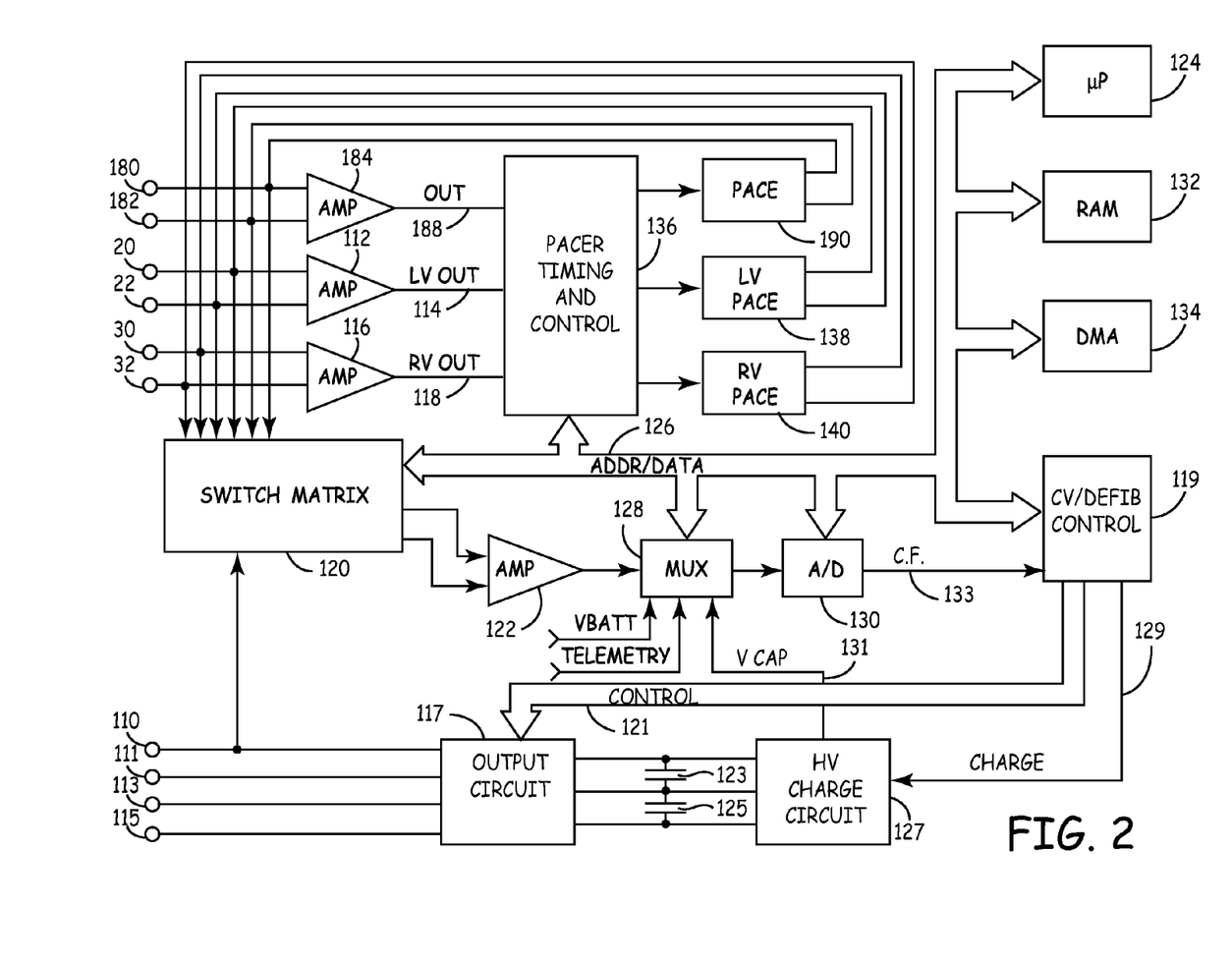
FIG. 2 is a functional block diagram of an IMD such as that shown in FIG. 1 comprising a pacemaker that includes both pacing and defibrillation functionality.

FIG. 2 is a functional block diagram of an embodiment of IMD 10, such as that shown in FIG. 1 in which IMD 10 comprises a pacemaker that include both pacing and defibrillation functionality. As shown in FIG. 2, IMD 10 includes an electrode system. Electrode 110 in FIG. 2 includes the uninsulated portion of housing 42 of IMD 10. Electrodes 110,111, 113,115 are positioned along one or more of leads 14,15,26 and are coupled to high voltage output circuit 117, which includes high voltage switches controlled by cardioversion/defibrillation (CV/defib) control logic 119 via control bus 121. Switches disposed within circuit 117 determine which electrodes are employed and which electrodes are coupled to the positive and negative terminals of the capacitor bank (which includes capacitors 123,125) during delivery of defibrillation pulses.

Capacitors 123,125 may have reduced size relative to conventional capacitors used in IMDs. In particular, a number of capacitor features are described in greater detail below, which can significantly reduce the volume associated with capacitors 123,125. Moreover, since capacitors 123,125 comprise a significant portion of the volume of IMD 10, reductions in capacitor volume can likewise significantly reduce the size of IMD 10.

Electrodes 20,22 may be located on or in left ventricle 24 of the patient and are coupled to amplifier 112, which may comprise an automatic gain controlled amplifier providing an adjustable sensing threshold as a function of the measured R-wave amplitude. For example, electrodes 20,22 may be positioned proximate to distal end left ventricular (LV) coronary sinus lead 14 (FIG. 1). A signal is generated on LV out line 114 whenever the signal sensed between electrodes 20 and 22 exceeds the present sensing threshold.

Electrodes 30,32 are located on or in right ventricle 28 of the patient and are coupled to amplifier 116. Electrodes 180, 182 conceptually represent electrodes located at any desired location within or in proximity to heart 12. Electrodes 180, 182 are coupled to amplifier 184. In one example, electrodes 180,182 may be positioned proximate to distal end of right atrium (RA) lead 15 (FIG. 1). However, in other embodiments, electrodes 180,182 may correspond to any other desired location. In many multi-site embodiments, pairs of electrodes are provided at a number of locations. In other embodiments, a number of pairs of electrodes may be used specifically for one chamber of the heart. In general, however, any number of pairs of electrodes may be deployed in a variety of locations around the heart. The invention, however, can be used in systems having any number of leads and any number of electrodes.

Switch matrix 120 is used to select which of the available electrodes are coupled to wide band (0.5-200 Hz) amplifier 122 for use in digital signal analysis. Selection of electrodes is controlled by microprocessor 124 via data/address bus 126, and the selections may be varied as desired. Signals from the electrodes selected for coupling to band pass amplifier 122 are provided to multiplexer 128, and thereafter converted to multi-bit digital signals by A/D converter 130, for storage in random access memory 132 under control of direct memory access circuit 134. Microprocessor 124 may employ digital signal analysis techniques to characterize the digitized signals stored in random access memory 132 to recognize and classify the patient's heart rhythm.

The remainder of the circuitry may be dedicated to cardiac pacing, cardioversion and defibrillation therapies in accordance with one or more embodiments of the invention. Pacer timing/control circuitry 136 includes programmable digital counters, which control the basic time intervals associated with modes of pacing. Circuitry 136 also controls escape intervals associated with pacing. Circuitry 136 also determines the amplitude of the cardiac pacing pulses under control of microprocessor 124.

During pacing, escape interval counters within pacer timing/control circuitry 136 may be reset upon sensing of R-waves as indicated by a signals on lines 114 and 118. In accordance with the selected mode of pacing, pacer timing/control circuitry 136 triggers generation of pacing pulses by pacer output circuitry 138,140 and 190 which are coupled to electrodes 20,22,30,32,180,182. Escape interval counters may also be reset on generation of pacing pulses and thereby control the basic timing of cardiac pacing functions. The durations of the intervals defined by escape interval timers are determined by microprocessor 124 via data/address bus 126.

In the event that generation of a cardioversion or defibrillation pulse is required, microprocessor 124 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 124 activates cardioversion/defibrillation control circuitry 119, which initiates charging of the high voltage capacitors 123,125 via charging circuit 127, under the control of high voltage charging control line 129. Again, capacitors 123,125 make use of capacitor designs described in greater detail below.

The voltage on the high voltage capacitors 123,125 is monitored via VCAP line 131, which is passed through multiplexer 128 and in response to reaching a predetermined value set by microprocessor 124, results in generation of a logic signal on Cap Full (CF) line 133 to terminate charging. Thereafter, timing of the delivery of the defibrillation or cardioversion pulse is controlled by pacer timing/control circuitry 136. Following delivery of the fibrillation or other arrhythmia therapy, microprocessor 124 returns the device to cardiac pacing mode and awaits the next successive interrupt due to pacing or the occurrence of a sensed atrial or ventricular depolarization.

Any cardioversion or defibrillation pulse control circuitry may be used in conjunction with various embodiments of the invention. By way of example, delivery of cardioversion or defibrillation pulses can be accomplished by output circuit 117 under the control of control circuitry 119 via control bus 121. Output circuit 117 determines whether a monophasic or biphasic pulse is delivered, the polarity of the electrodes, and which electrodes are involved in delivery of the pulse. Output circuit 117 also includes high voltage switches, which control whether electrodes are coupled together during delivery of the pulse. Alternatively, electrodes intended to be coupled together during the pulse may simply be permanently coupled to one another, either exterior to or interior of the device housing, and polarity may be pre-set.

The embodiment shown in FIG. 2 is merely exemplary. For example, the embodiment shown in FIG. 2 may be modified to include additional features, or may be adapted to other embodiments. In particular, the embodiment in FIG. 2 may be modified for an implanted medical device having electrodes mounted on any number of leads not shown in FIG. 1, or may not include one or more of the leads shown in FIG. 1. Such electrodes may be coupled to a P-wave amplifier (not shown in FIG. 2) that, like amplifiers 112 an 116, provides an adjustable sensing threshold as a function of a measured P-wave amplitude. The embodiment shown in FIG. 2 may further be modified to detect activity in or near the left atrium of the patient and may include physiologic transducers (e.g., mechanical, metabolic and/or electrically-based sensors).

Microprocessor 124 performs mathematical calculations to carry out arrhythmia detection and therapy algorithms known in the art of cardiac pacing. The invention may find wide application to any form of implantable electrical device or possibly external medical devices that make use of high voltage capacitors.

In accordance with the invention, IMD 10 makes use of capacitors that have reduced volume relative to conventional capacitors. In the description that follows, capacitors are described as including one or more features that can help achieve such volume reduction. The capacitors described with reference to FIGS. 3-4 and 6-7, for example, may be implemented as capacitors 123 and 125 of IMD 10 described above, or may find use in a wide variety of other types of medical devices. The invention may be most useful in applications where size is a concern, although the invention is not necessarily limited in that respect.

Figure 3:
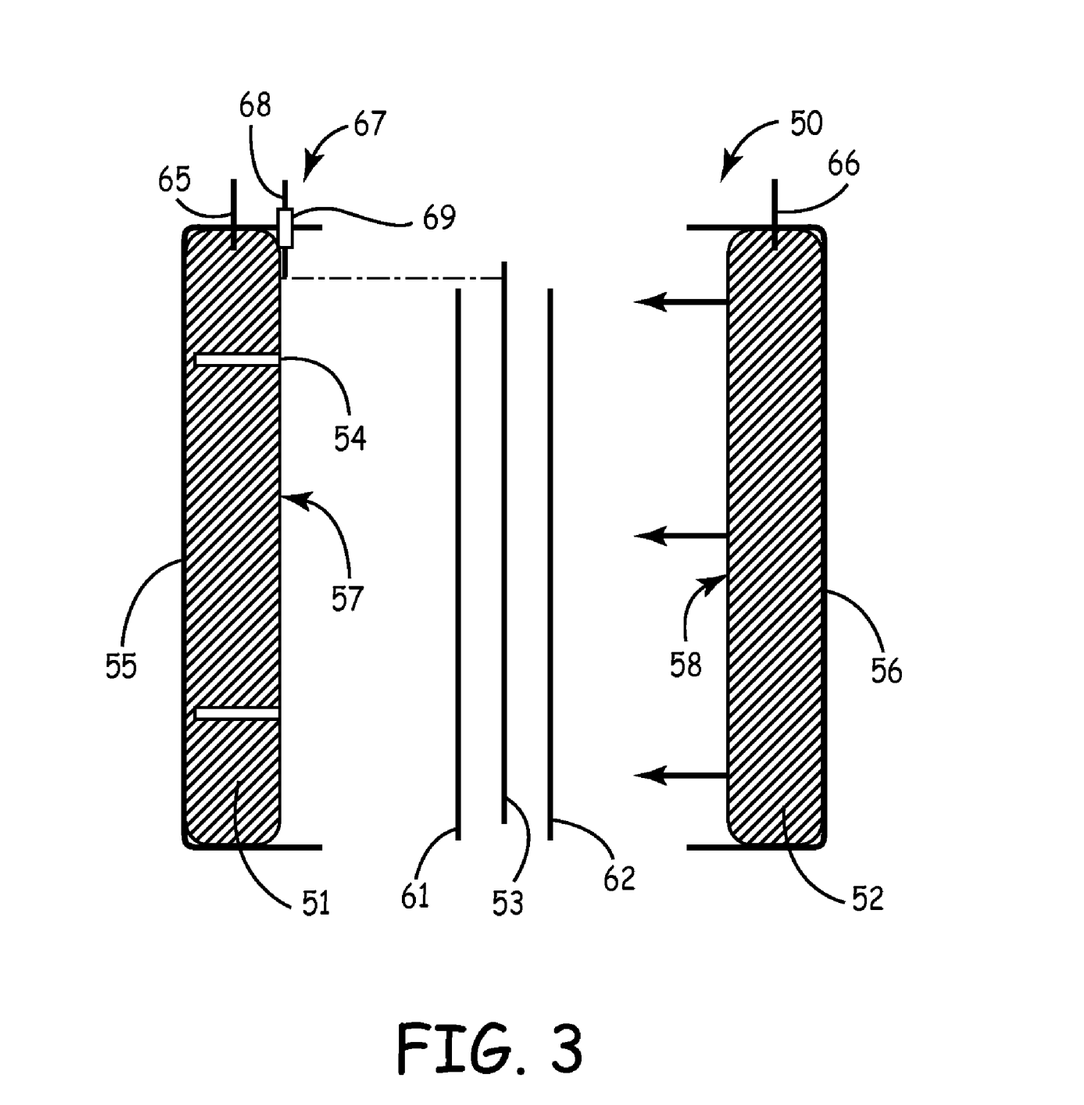
FIG. 3 is an exploded cross-sectional view of a capacitor according to an embodiment of the invention.
Figure 4:
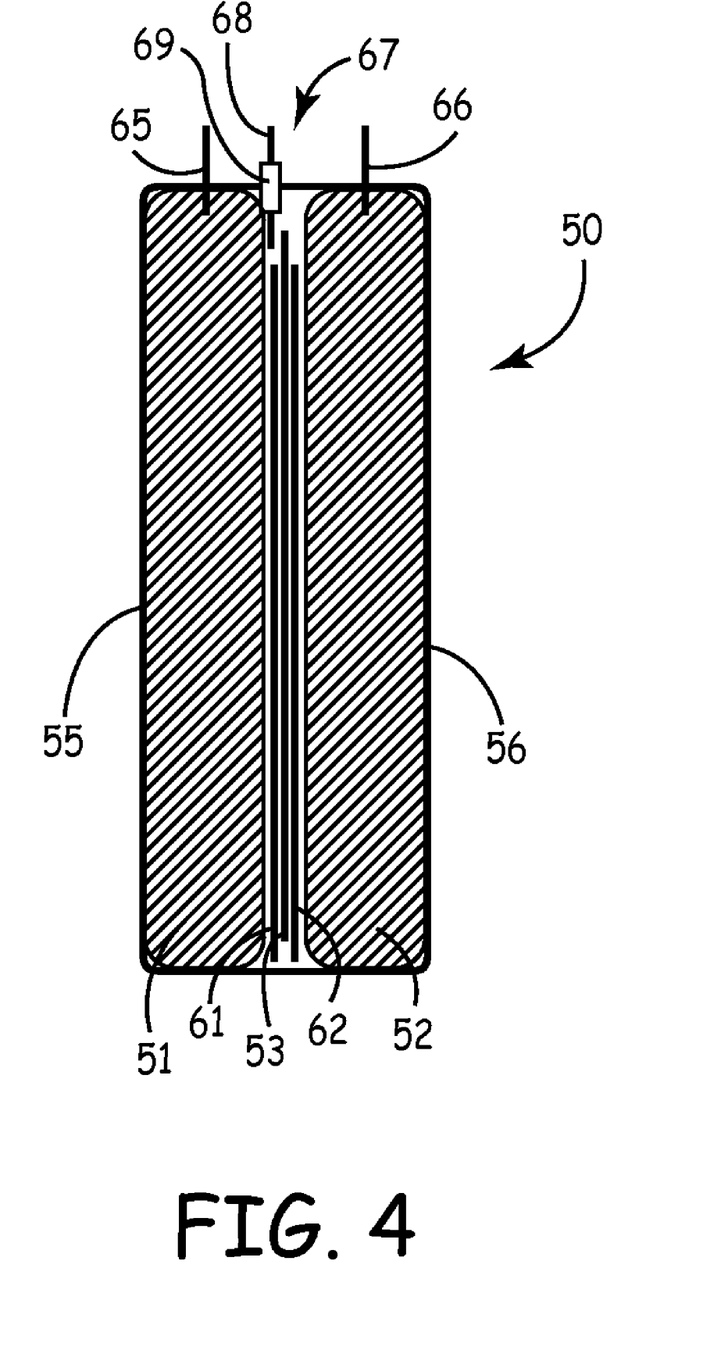
FIG. 4 is an assembled cross-sectional view of the capacitor illustrated in FIG. 3.

FIG. 3 is an exploded cross-sectional view of a capacitor 50, which may correspond to either of capacitors 123,125 (FIG. 2). FIG. 4 is an assembled cross-sectional view of capacitor 50. Capacitor 50 comprises a sandwiched construction case-positive design in which two anodes 51,52 sandwich a cathode 53. In particular, following construction and assembly (as shown in FIG. 4), capacitor 50 comprises a first anode 51 constructed within a first encasement shell 55 and a second anode 52 constructed within a second encasement shell 52. The anodes 51,52 may be in intimate contact, and therefore electrical, with first and second encasement shells 55,56, and the encasement shells 55,56 may or may not form part of the anodes 51,52. For example, anodes 51,52 can be formed by pressing tantalum powder into encasement shells 55,56. The encasement shells 55,56 may comprise tantalum encasement shells having U-shaped cross sections of different depths. Optionally, a press, multi-faceted mold, and/or a drill may be used to form tunnels, bores and/or holes in anodes 51,52 during construction, which can help heat dissipation during formation and may also reduce equivalent series resistance (ESR) during use of capacitor 50. As is known in the art, following such processing an oxide layer is generated during formation when anodes 51,52 are immersed in a pool of formation electrolyte while electrical potential is applied until a desired formation voltage (and oxide thickness) is achieved. In the case anodes 51,52 are formed from pure tantalum powder, a layer of tantalum pentoxide is formed to a desired voltage (e.g., 175 to over 200 volts).

Cathode 53 is sandwiched between first and second anodes 51,52 within first and second encasement shells 55,56. In addition, separator material 61,62 is sandwiched between the first and second anodes 51,52 within the first and second encasement shells 55,56 in order to electrically separate cathode 53 from anodes 51,52. The separator material can comprise cellulose material such as Kraft paper and the like but, in general, the separator material needs to allow ion transport between the anodes 51,52 and cathode 53.

In accordance with the invention, the capacitor construction illustrated in FIGS. 3 and 4 may allow for significant reductions in non-charge storing material such as separator materials 61,62 relative to conventional capacitor designs. In particular, the capacitor construction illustrated in FIGS. 3 and 4 may allow for energy storing components such as anodes 51,52 to comprise greater than 70 percent, greater than 80 percent, or even greater than 85 percent of the volume of capacitor 50. In other words, the amount of material forming anodes 51,52 can form an increased percentage of the total volume of capacitor 50. Accordingly, relative to conventional capacitor designs that are less efficient, capacitor 50 may have reduced volume, or may achieve increased energy storage capacity with a volume similar to that of such conventional designs.

Electrical contact pins may be formed in capacitor 50 to facilitate electrical connection to anodes 51,52 and cathode 53. For example, a first electrical anode pin 65 can be formed through first encasement shell 55 for electrical contact with first anode 51, and a second electrical anode pin 66 can be formed through the second encasement shell 56 for electrical contact with second anode 52. In order to facilitate electrical contact to cathode 53, a feedthrough element 67 can be formed through one of the encasement shells (in this case shell 55). The feedthrough element 67 may include a cathode pin 68 within an insulative material 69 for electrical contact to cathode 53. Insulative material 69 may comprise glass, or some other suitable insulator. Following assembly, cathode pin 68 may electrically couple to cathode 53 and provide external electrical access to cathode 53 as illustrated in FIG. 4.

In order to simplify construction of capacitor 50, first encasement shell 55 can be made deeper than the second encasement shell 56. Accordingly, when cathode 53 is sandwiched between first and second anodes 51,52 within first and second encasement shells 55,56, the first encasement shell 55 overlaps second anode 52 to abut against second encasement shell 56. In that case, feedthrough element 67 can be formed through first encasement shell 55 in order to achieve proper placement of cathode pin 68 relative to cathode 53, following assembly of capacitor 50.

In some cases, anodes 51,52 can provide structural support to capacitor 50. By providing structural support via anodes 51,52, the mass of encasement shells 55,56 may be reduced, which can reduce the size of improve capacitor 50. In some embodiments, anodes 51,52 can provide more structural support to capacitor 50 than encasement shells 55,56. In order to improve such structural support of anodes 51,52, one or more structural enhancing elements can be formed within anodes 51,52. For example, the structural enhancing elements may comprise electrode wires formed within anodes 51,52, or any other structural enhancing element that would not significantly undermine the charge holding capacity of anodes 51,52.

For a wet-type capacitor 50 the enclosure is filled with a working electrolyte (not shown) that typically differs from the formation electrolyte. One fairly common working electrolyte comprises a sulfuric acid/glycol base electrolyte. In addition, if desired, a substantially non-permeable film (not shown) can be formed over capacitor 50, e.g., to improve a hermetic barrier to the interior of capacitor 50. In that case, anode pins 65, 66 and cathode pin 68 may pass through the substantially non-permeable film. Alternatively, capacitor 50 may be packaged in a foil pack, an insulated metal case, or any other suitable packaging material.

Figure 5:
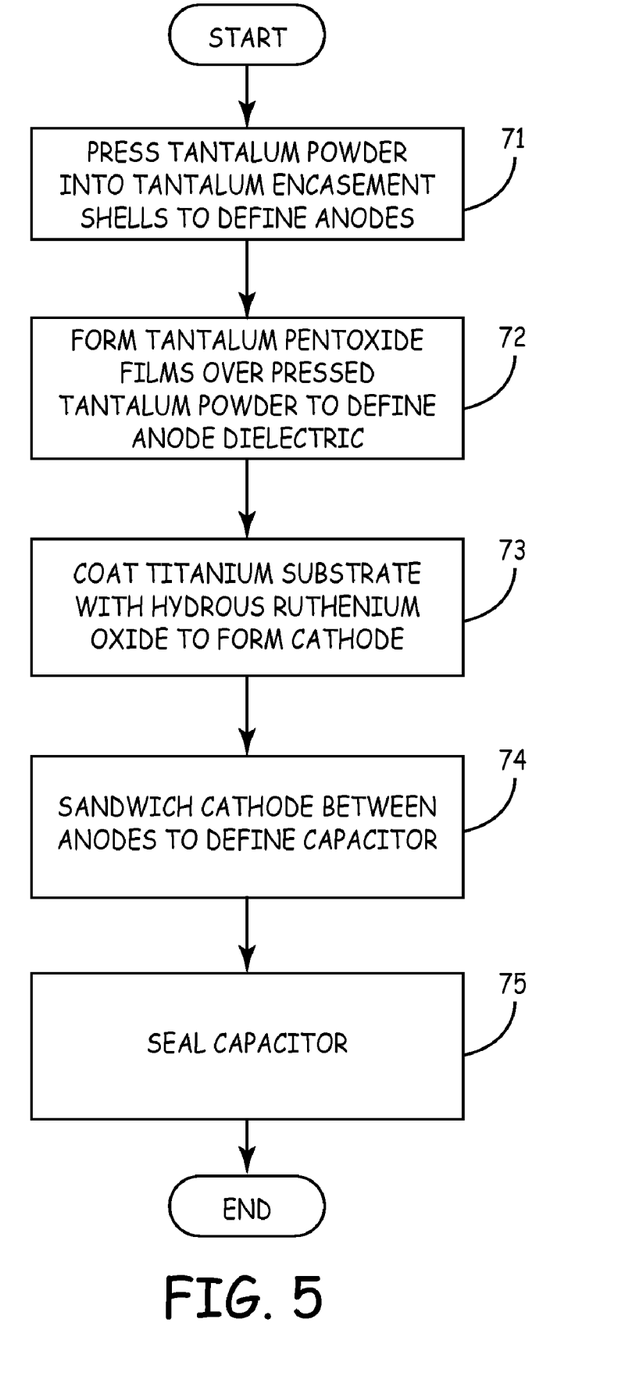
FIG. 5 is a flow diagram illustrating a process for fabricating the capacitor illustrated in FIGS. 3 and 4.

FIG. 5 is a flow diagram illustrating some of the steps for a process for creating capacitor 50. As shown in FIG. 5, a tantalum powder is pressed into tantalum encasement shells 55,56 to define a pair of anode slugs 51,52 (71). In some cases, the press used to create anodes 51,52 creates a series of tunnels or holes 54 in the anodes in order to aid in heat dissipation during the forming process and reduce ESR during operation. Optionally, one or more structural enhancing materials may be dispersed throughout the metallic powder prior to pressing the anode. Such materials are known as binders or binding agents and they are used primarily to provide increased structural integrity and to provide a changing density "gradient" to interior portions of anodes 51,52 during pressing. Such material can be used to control expansion, shrinkage or shape deformation. Such materials are preferably completely removed after pressing (prior to, during or after sintering). Thus, a suitable binder can be susceptible of complete removal simply as a result of the high temperature, high pressure sintering processing. In addition to or in lieu of the foregoing suitable material can be susceptible of completely dissolving in a fluid bath. The anodes are sintered prior to forming the tantalum pentoxide film over surfaces 57, 58. A tantalum pentoxide film is then formed on anodes 51,52, e.g., over surfaces 57, 58 to define the anode dielectric for anodes 51,52 (72). Although a specific sintering step is not depicted in FIG. 5, the present invention does not depend on a particular mode of sintering and those of skill in the art will apply appropriate temperatures and pressures to suitably sinter an anode slug.

A cathode substrate is coated on opposing sides with hydrous ruthenium oxide, activated carbon, or other suitable cathode-active material(s) to form cathode 53 (73). In the illustrated and described embodiments, the cathode substrate comprises a titanium member. Said titanium member may be substantially flat, perforated and/or surfaced with minute features to enhance the bond with the cathode-active material. Cathode 53 is then sandwiched between anodes 51,52 to define capacitor 50 (74). Separator material 61,62 may be provided to electrically isolate cathode 53 from anodes 51,52 in the final construction of capacitor 50. Of course, while separator material 61,62 is depicted as individual members, a single sheet portion (or more than one sheet) of separator material may be used to essentially wrap and thereby insulate the cathode 53. In the final construction of capacitor 50, an electrical contact pin 68 of feedthrough 67 may contact cathode 53 to provide electrical access to cathode 53. In order to aid such a construction, tantalum encasement shells 55,56 may define U-shaped cross-sections in which shell 55 is deeper than shell 56, and includes feedthrough 67 in proper alignment with cathode 53. If desired, a laser weld or solder may be used to couple encasement shells 55,56 to one another where they abut one another.

Capacitor 50 is then sealed (75). Sealing capacitor 50 may comprise filling any voids in capacitor 50 with a sulfuric acid/glycol base electrolyte, e.g., through a fillport formed in one of shells 55,56. The electrolyte can be aged and possibly cured to form and repair dielectric material in capacitor 50. In addition, sealing capacitor 50 may further comprise re-filling capacitor 50 with electrolyte, and sealing a fillport used to inject the electrolyte, thereby forming a hermetically sealed capacitor 50. If desired, a substantially non-permeable film can also be formed over capacitor 50 to improve the hermetic barrier to the interior of capacitor 50. In that case, anode pins 65,66 and cathode pin 68 may pass through the substantially non-permeable film. Alternatively, capacitor 50 may be packaged in a foil pack, an insulated metal case, or any other packaging material.

Capacitor 50 may provide one or more advantages, particularly when used in an IMD similar to that illustrated in FIGS. 1 and 2. In particular, capacitor 50 may achieve reduced volume relative to conventional capacitor constructions. Alternatively, the same volume of capacitor 50 relative to conventional designs may achieve improved energy storage capacity. In particular, the efficiency of capacitor 50, i.e., the percentage of volume used for energy storage may be greater than 70 percent, greater than 80 percent, or even greater than 85 percent. Such efficiency may be related to one of several factors, including the case positive anode-cathode-anode design, reduced amounts of separator material 61,62, reduced structural requirements of shells 55,56, increased structural integrity of anodes 51,52 and the specific materials used in the construction.

Figure 6:
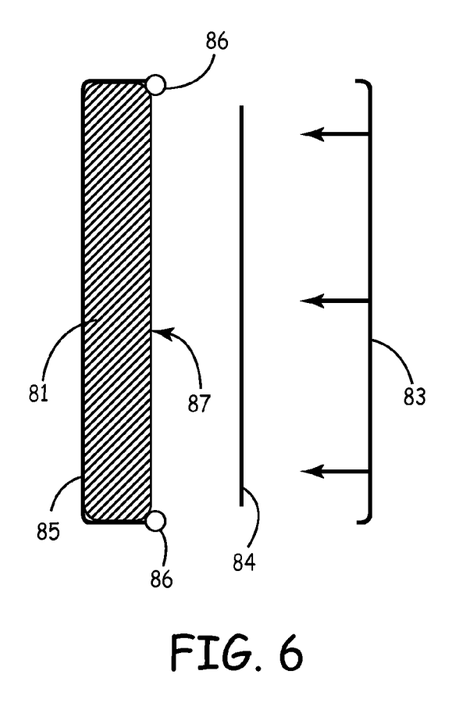
FIG. 6 is an exploded cross-sectional view of another capacitor according to another embodiment of the invention.
Figure 7:
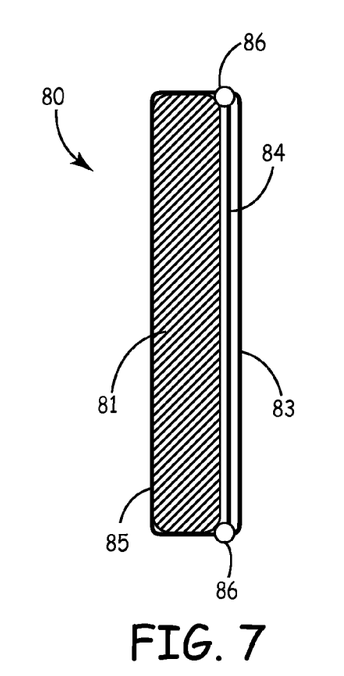
FIG. 7 is an assembled cross-sectional view of the capacitor illustrated in FIG. 6.

FIGS. 6 and 7 illustrate another embodiment of the invention in which capacitor 80 comprises a bi-polar case capacitor. In particular, FIG. 6 is an exploded cross-sectional view of a capacitor 80, and FIG. 7 is an assembled cross-sectional view of capacitor 80. Capacitor 80 may correspond to either of capacitors 123,125 (FIG. 2). Capacitor 80 comprises a single anode 81 formed in a manner similar to the formation of anodes 51,52, described above. For example, anode 81 can be formed by pressing tantalum powder into encasement shell 85, which may or may not form part of anode 81. Anode 81 may be in intimate contact with encasement shell 85. Encasement shell 85 may comprise a tantalum encasement shell having a U-shaped cross section. Optionally, a press may be used to form tunnels or holes in anode 81 prior to forming the oxide layer on the anodes 51,52.

Capacitor 80 also includes a single cathode 83 forming an opposing side of the case structure. In particular, cathode 83 can be formed in a manner similar to the creation of cathode 53, described above, e.g., a titanium substrate can be coated on opposing sides of the titanium substrate with hydrous ruthenium oxide, activated carbon, titanium carbide, etc. to form cathode 83. However, in this case, cathode 83 is not sandwiched between anodes, but instead forms an opposing encasement shell of capacitor 80, i.e., the shell that opposes shell 85. A separator material 84 can be sandwiched between anode 81 and cathode 83. Moreover, at the interface of encasement shell 85 and cathode 83 an insulative material 86 is used to electrically isolate anode 81 from cathode 83. A laser weld or solder may be used to couple encasement shell 85 and cathode 83 to insulative material 86. Electrical contact to anode 81 and cathode 83 may be made via contact with the outer surfaces of capacitor 80.

Figure 8:
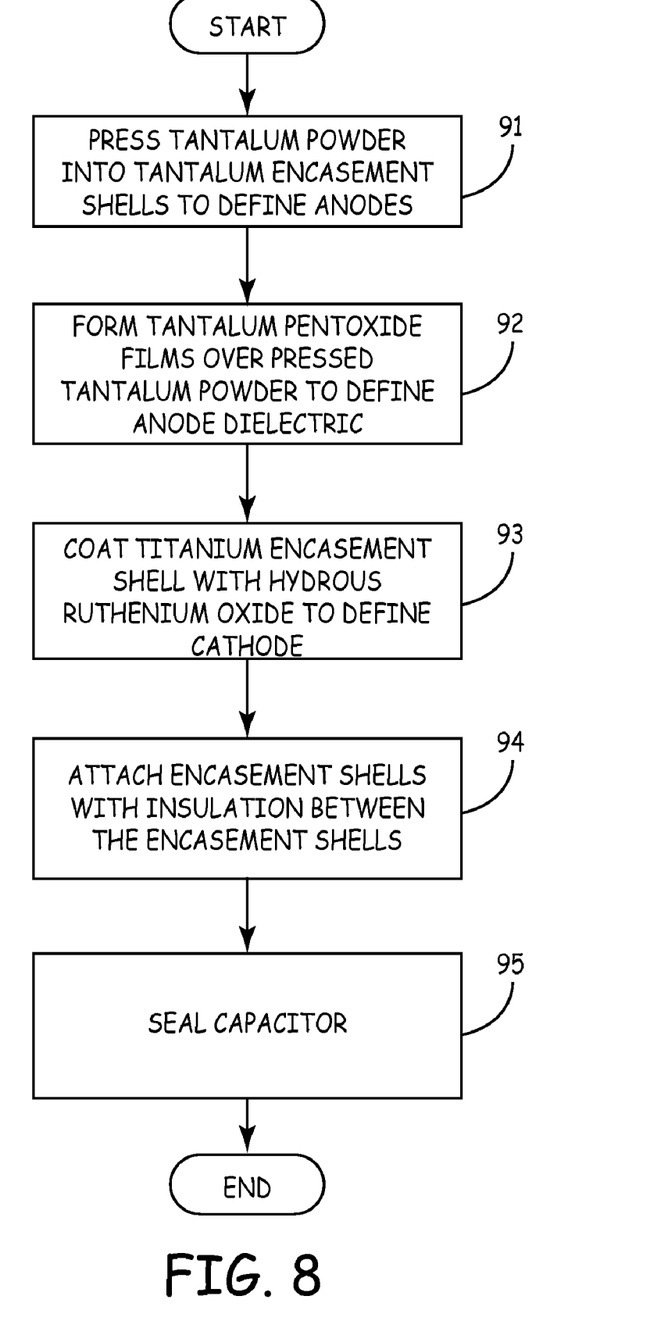
FIG. 8 is a flow diagram illustrating a process for creating the capacitor illustrated in FIGS. 6 and 7.

FIG. 8 is a flow diagram illustrating creation of capacitor 80 having a bipolar case capacitor design. As shown in FIG. 8, a tantalum powder is pressed into tantalum encasement shell 85 to define anode 81 (91). In some cases, the press used to create anode 81 creates a series of tunnels or holes in anode 81 in order to aid in heat dissipation during the forming process and reduce ESR during operation. Also, one or more structural enhancing elements may be provided within the tantalum powder during pressing, in order to give anode 81 increased structural integrity. Again, similar to FIG. 5, FIG. 8 is devoid of specific illustration regarding the sintering of the anodes. As earlier stated, those of skill in the art will readily appreciate the necessary temperature and pressure settings for appropriate sintering. Notably, however, as earlier described and herein claims, the sintering occurs to both the pressed tantalum powder anode and the enclosure therefore. A tantalum pentoxide film is then formed over surfaces 87 to define the anode dielectric for anode 81 (92).

A titanium encasement shell is coated with hydrous ruthenium oxide to form cathode 83 (93). Encasement shell 85 and cathode 83, which forms the opposing encasement shell, are then attached to one another (94). Insulation 86 is provided at the interface of encasement shell 85 and cathode 83 for electrical isolation of cathode 83 and anode 81. Separator material 84 may also be provided to electrically isolate cathode 83 from anode 81 in the final construction of capacitor 80.

Capacitor 80 is then sealed (95). Sealing capacitor 80 may comprise filling any voids in capacitor 80 with a sulfuric acid/glycol base electrolyte, e.g., through a fillport formed in one of shell 85 and cathode 83. The electrolyte can be aged or cured to form and repair dielectric material in capacitor 80. In addition, sealing capacitor 80 may further comprise re-filling capacitor 80 with electrolyte, and sealing a fillport used to inject the electrolyte in order to form a hermetically sealed capacitor 80. If desired, capacitor 50 may be further packaged in a film, foil, metal case, or any other packaging material.

A number of capacitor designs for use in medical devices have been described. The capacitors may find application any of a wide variety of medical devices, but are most useful in applications where size is a concern. Nevertheless, various modifications may be made without departing from the scope of the following claims. For example, the capacitors may be used in numerous other devices, and may be specifically desirable for applications where small-volume, high voltage capacitors are desired. Non-medical device applications are also envisioned. These and other embodiments are within the scope of the following claims.

The invention claimed is:

1. A medical device including circuitry to control delivery of a high voltage electrical therapy to a patient and an electrolytic capacitor to store charge for use in the delivery of the high voltage electrical therapy, comprising:
    a first anode mechanically coupled to and electrochemically anodized within a first encasement shell;
    a second anode mechanically coupled to and electrochemically anodized within a second encasement shell; and
    a cathode disposed between the first anode and the second anode and within the first and second encasement shells.

2. A medical device according to claim 1, the capacitor further comprising separator material sandwiched between the first and second anodes and within the first and second encasement shells to electrically separate the cathode from the anodes.

3. A medical device according to claim 1, the capacitor further comprising:
    a first electrical anode pin formed through the first encasement shell for electrical contact with the first anode;
    a second electrical anode pin formed through the second encasement shell for electrical contact with the second anode; and
    a feedthrough element formed through one of the encasement shells, the feedthrough element including a cathode pin within an insulative material for electrical contact to the cathode.

4. A medical device according to claim 1, wherein the first encasement shell has a greater volumetric dimension than the second encasement shell such that when the cathode is sandwiched between the first and second anodes and within the first and second encasement shells, the first encasement shell overlaps the second anode to abut against the second encasement shell.

5. A medical device according to claim 1, wherein the first anode and the second anode provides greater structural support to the capacitor than the encasement shells.

6. A medical device according to claim 1, wherein the encasement shells comprise tantalum and the anodes comprise tantalum powder pressed within the encasement shells and anodized to provide a layer film of tantalum pentoxide on exposed surfaces of said anodes.

7. A medical device according to claim 6, wherein the cathode comprises a titanium substrate coated on opposing sides with hydrous ruthenium oxide.

8. A medical device according to claim 1, wherein the anodes comprise one or more holes formed in the anode to aid in heat dissipation.

9. A medical device according to claim 1, the capacitor further comprising a substantially non-permeable film formed over the capacitor and electrical contacts to the anodes and cathode, wherein the electrical contacts to the anodes and cathode pass through the substantially non-permeable film.

10. A medical device including circuitry to control delivery of a high voltage electrical therapy to a patient and an electrolytic capacitor to store charge for use in the delivery of electrical therapy, comprising:
    an anode mechanically coupled to and electrochemically anodized within a first encasement shell;
    a cathode forming a second encasement shell; and
    insulative material disposed at an interface of the first and second encasement shells to electrically isolate the anode from the cathode.

11. A medical device according to claim 10, the capacitor further comprising a separator material sandwiched between the first and second encasement shells to electrically separate the cathode from the anode.

12. A medical device according to claim 10, the capacitor further comprising one or more structural enhancing elements within the anode.

13. A medical device according to claim 10, wherein the first encasement shell comprises tantalum and the anode comprise tantalum powder pressed within the first encasement shell and covered with a film of tantalum pentoxide.

14. A medical device according to claim 13, wherein the second encasement shell comprises a titanium substrate coated on opposing sides of the titanium substrate with hydrous ruthenium oxide.

15. The medical device of claim 1 further comprising at least one additional cathode and at least one additional anode, a total number of cathodes and a total number of anodes present in a ratio of the total number of anodes to the total number of cathodes of greater than 1:1.

16. A medical device including circuitry to control delivery of electrical therapy to a patient and a capacitor to store charge for use in the delivery of electrical therapy, comprising:
 a first anode coupled to a first encasement shell;
 a second anode within a second encasement shell; and
 a cathode disposed between the first anode and the second anode and within the first and second encasement shells.

17. A medical device including circuitry to control delivery of a high voltage electrical therapy to a patient and an electrolytic capacitor to store charge for use in the delivery of the high voltage electrical therapy, comprising:
 a first anode mechanically coupled to and electrochemically anodized within
 a first encasement shell, the first anode in intimate contact with the first encasement shell;
 a second anode mechanically coupled to and electrochemically anodized within a second encasement shell, the second anode in intimate contact with the second encasement shell; and
 a cathode disposed between the first anode and the second anode and within the first and second encasement shells.

18. The medical device of claim 17 wherein the first anode being electrically coupled to the first encasement shell and the second anode being electrically coupled to the second encasement shell.

\* \* \* \* \*